July 18, 1950 J. VETTER Plant Pat. 966
PEACH TREE
Filed May 23, 1949
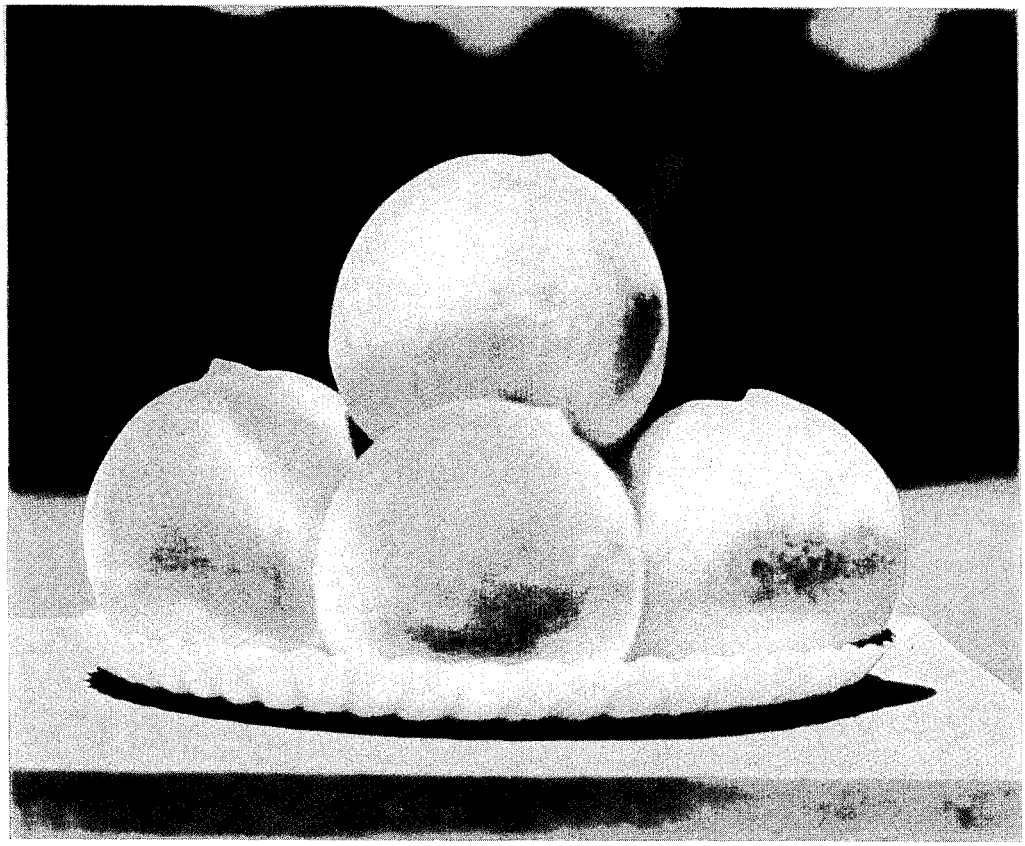
Inventor
J. Vetter
By Robert Robb
Attorney Patented July 18, 1950

Plant Pat. 966

UNITED STATES PATENT OFFICE

966

PEACH TREE

Joseph Vetter, Reedley, Calif., assignor of one-half to Roy Huth, trading as West Visalia Nursery, Visalia, Calif.

Application May 23, 1949, Serial No. 94,759

1 Claim. (Cl. 47—62)

The present discovery relates to a new and distinct variety of peach tree, originating as a sport of the well-known "July Elberta" peach and characterized as to novelty dominantly by its habits of growth, its later blooming period, color, keeping quality and aroma of the fruit, as compared with the parent.

Since this new variety resembles its parent variety more closely than any other known to me, a specific comparison therewith is desirable to show its distinctiveness, before discussing which it may be noted that I discovered the variety in my orchard of all "July Elbertas," it appearing as as mutation on the north half of a certain tree, blooming ten to fourteen days later than the south half.

Comparing the original sport and its progeny with "July Elberta," I noted its similarity of growth as a strong and upright tree, but it bore stronger and heavier branches and heavier foliage, the latter being deeper in color and possessing good resistance to damage from winds and bad weather, and better resistance to disease and insects than the parent.

However, the most important distinguishing features are its late blooming period (about four weeks later than "July Elberta" when grown under comparable conditions), which insures safety against bad weather; its heavier setting of fruit; little better sizing and color on an average; more roundness in shape and having a more delightful aroma and flavor. The aroma is somewhat like that of the "Le Grand" and "Quetta" varieties. While above stated, the new variety blooms later, it ripens about three weeks earlier than the parent variety when grown under comparable conditions.

These characteristics come true to form in the progeny and are established.

In the drawing are illustrated specimens of the fruit, showing as nearly as can be depicted the shape and color characteristics.

The following is a detailed description of the new variety, color terminology being in accordance with ordinary dictionary significance:

The specimens described were grown, and asexually reproduced by grafting, in Tulare County, California.

Dates first and last picking—approximately June 5th and June 15th.

*Tree*

Medium size; vigorous; upright; open; vase formed; hardy; very productive; regular bearer.

Trunk: Medium stocky; smooth.

Branches: Medium stocky, smooth; brown-gray; dull.

*Lenticels.*—Medium number; medium size.

Leaves:

*Length.*—Six inches.

*Width.*—Average ⅞ inch. Large; obovate; lanceolate; acutely pointed; thick; dark green; rugose.

*Margin.*—Finely serrate.

*Petiole.*—Medium length; medium thick.

*Glands.*—Four to each leaf; opposite; medium size; globose; greenish yellow; position on very base of leaf.

*Stipules.*—None.

Flower buds: Hardy; medium size; medium length; plump; free; pubescent.

Flowers: Dates first bloom—March 8th, and full bloom March 15th. Late compared with other varieties. Medium size; Salmon.

*Fruit*

In normal seasons, commencing to ripen the 2nd of June—good or best eating condition June 8th–10th.

Size: Medium.

*Diameter axial.*—2¾ inches to 3½ inches.

*Transverse in suture plane.*—2½ inches to 2¾ inches.

*At right angles to suture plane.*—2¾ inches to 3 inches.

Form: Uniform; globose; oblate.

*Suture.*—Extends from base to beyond but discontinuous at apex over entire circumference.

*Ventral surface.*—Lipped toward base throughout both sides. Lips—equal to unequal.

*Cavity.*—Rounded; elongated in suture plane with suture showing on one side. Depth, ⅜ inch; breadth, ½ inch. Marking—none.

*Base.*—Rounded.

*Apex.*—Short; mammiform. Pistil point—apical.

*Stem.*—Length ⅜ inch; stout; glabrous. Adherence to stone—strong.

*Skin.*—Medium thick; tenacious to flesh. Tendency to crack—none in wet season. Color—Yellow with considerable red blush. Down—scant; does not roll up when rubbed; short.

Flesh:

*Color.*—Yellow, with yellowish tinge. Surface of pit cavity—Yellow. Fibres—few.

*Amygadalin.*—Scant. Juice—scant.

*Texture.*—Fine; meaty.

3

*Fibres.*—Few; tender.
*Ripens.*—Even; earliest at apex along both lips.
*Flavor.*—Subacid.
*Aroma.*—Pronounced.
*Eating quality.*—Best.

Stone: Semifree; adheres to flesh over entire surface along both dorsal and ventral edges over upper half of sides; fibres short; free on sides toward base; parts from flesh smoothly; retains short fibre-like threads along ridges.
*Size.*—Average. Length, 1½ inches; breadth, 1 inch; thickness, ¾ inch.
*Form.*—Oblong; oval.
*Base.*—Hilum—oval. Apex—acute.
*Sides.*—Equal. Surface—regularly furrowed near base; ridged near base toward apex.
*Ridges.*—Rounded.
*Pits.*—Elongated. Ventral edge—thin; with wing toward base throughout.

4

*Dorsal edge.*—Narrow. Ridges—on either side interrupted.
*Color of stone.*—Lemon Yellow.
*Tendency to split.*—Not at all.

Use: Particularly for dessert but good for practically all uses.
Keeping quality: Good.
Resistance to: Insects and diseases—good.
Shipping quality: Good.

I claim:

A new and distinct variety of peach tree, characterized as to novelty by its late blooming but early ripening habits; its heavier setting of fruit, better size and deeper color, rounder shape, more delightful aroma and flavor than its parent variety; and better keeping and shipping quality, substantially as shown and described.

JOSEPH VETTER.

No references cited.